United States Patent
James et al.

(10) Patent No.: US 6,711,940 B2
(45) Date of Patent: Mar. 30, 2004

(54) METHOD AND APPARATUS FOR MEASURING THE ELASTICITY OF FLUIDS

(76) Inventors: David James, 7 Edmund Ave., Apt. 610, Toronto, Ontario M4V 1H2 (CA); Thayananthan Yogachandran, 17 Wantanopa Crescent, Scarborough, Ontario M1H 2B2 (CA)

( * ) Notice: Subject to any disclaimer, the term of this patent is extended or adjusted under 35 U.S.C. 154(b) by 0 days.

(21) Appl. No.: 10/188,919

(22) Filed: Jul. 5, 2002

(65) Prior Publication Data

US 2003/0051533 A1 Mar. 20, 2003

Related U.S. Application Data

(60) Provisional application No. 60/302,651, filed on Jul. 5, 2001.

(51) Int. Cl.[7] .............................................. G01N 11/00
(52) U.S. Cl. ..................... 73/53.01; 73/54.01; 73/54.02; 73/54.07
(58) Field of Search ............................. 73/53.01, 54.01, 73/54.07, 54.02, 53.04, 54.11, 64.49, 64.48

(56) References Cited

U.S. PATENT DOCUMENTS

| | | | | |
|---|---|---|---|---|
| 2,880,611 A | * | 4/1959 | Herren | 73/53.01 |
| 3,096,642 A | * | 7/1963 | Peterson | 73/53.01 |
| 3,415,109 A | * | 12/1968 | Sucker et al. | 73/64.49 |
| 4,072,045 A | * | 2/1978 | Kopito | 73/54.01 |
| 4,403,502 A | * | 9/1983 | Lindt | 73/55 |
| 4,437,337 A | * | 3/1984 | Fenrick | 73/54.01 |
| H093 H | * | 7/1986 | Matta et al. | 73/53.01 |
| 4,893,500 A | * | 1/1990 | Fink-Jensen | 73/60 |
| H976 H | * | 11/1991 | Matta et al. | 73/54.01 |
| 5,212,981 A | * | 5/1993 | Laun et al. | 73/54.01 |
| 5,269,174 A | * | 12/1993 | Chiba et al. | 73/54.01 |
| 5,456,105 A | * | 10/1995 | James | 73/54.01 |
| 5,457,987 A | * | 10/1995 | Bulou et al. | 73/64.49 |
| 5,705,738 A | * | 1/1998 | Kurihara | 73/54.39 |
| 5,744,703 A | * | 4/1998 | Krenceski et al. | 73/54.01 |
| 5,750,884 A | * | 5/1998 | Field | 73/54.24 |
| 5,792,941 A | * | 8/1998 | Rye et al. | 73/53.01 |
| 5,900,539 A | * | 5/1999 | Tremblay et al. | 73/54.13 |
| 6,098,450 A | * | 8/2000 | Willenbacher et al. | 73/54.01 |
| 6,119,511 A | * | 9/2000 | Christian et al. | 73/64.48 |

* cited by examiner

Primary Examiner—Hezron Williams
Assistant Examiner—Rodney Frank
(74) Attorney, Agent, or Firm—John R. S. Orange; Santosh K. Chari; Linda Kurdydyk

(57) ABSTRACT

An indication of the elasticity of a non-Newtonian fluid is obtained by extending a fluid bridge between a pair of relatively movable surfaces that hold a fluid sample therebetween, and continuing a timewise progression of separation between two opposed moveable surfaces in a controlled manner until the displacing extension is great enough to cause a break point in the fluid sample. The extension of a fluid bridge at the break point is determined and used as an indication of elasticity.

12 Claims, 10 Drawing Sheets

METHOD AND APPARATUS FOR MEASURING THE ELASTICITY OF FLUIDS

This application claims the benefit of provisional application No. 60/302,651 filed on Jul. 05, 2001.

FIELD OF THE INVENTION

The invention relates to a method and apparatus for measuring the elasticity of fluids.

BACKGROUND OF THE INVENTION

The elasticity of a material is defined in terms of its ability to return to its original shape after being deformed. Certain fluids possess elasticity as well as viscosity. For example, water is viscous and inelastic but shampoo, ink and paint are generally both viscous and elastic.

In many applications, it is desirable to measure the elasticity of a fluid. For example, an ink's ability to penetrate paper is affected by the ink's elasticity. A paint's tendency to drip is related to its elasticity. An evidence of elasticity in a liquid is the "stringiness" of the fluid.

A device for measuring extensional properties of fluids is a filament-stretching rheometer. This device stretches a fluid at a constant extensional rate, which means that the length of the filament increases exponentially with time. A filament-stretching rheometer comprises a diameter measuring system, a force transducer, a fluid sample, and an actuator. The fluid is held between an upper and a lower plate, the upper plate being attached to the force transducer, and the lower plate being connected to the actuator.

The actuator moves the lower plate away from the top plate in order to achieve a constant extensional rate while the force transducer measures the force exerted on the filament. Meanwhile, the diameter measuring system provides measurements of the diameter of the fluid filament at its mid point. From the measurements of force and diameter, the stress on the filament can be computed. These measurements may be used to determine the elasticity of the fluid.

However, a filament-stretching rheometer can generally be used only for fluids with relatively high elasticity. The magnitude of the forces incurred when testing liquids having relatively low elasticity, such as shampoo and ink, is much smaller and the resolution of, the noise in, the force transducer make it extremely difficult to obtain accurate measurements of the force on the filament.

It is therefore an object of the present invention to provide a method and apparatus that obviates or mitigates some of the above disadvantages.

SUMMARY OF THE INVENTION

The present invention is based upon the recognition that a measurement of the extension of the fluid at the break point may be used as an indication of the elasticity of the fluid.

BRIEF DESCRIPTION OF THE DRAWINGS

These and other features of the preferred embodiments of the invention will become more apparent in the following detailed description in which reference is made by way of example only to the appended drawings wherein.

DESCRIPTION OF THE PREFERRED EMBODIMENTS

Figure 1:
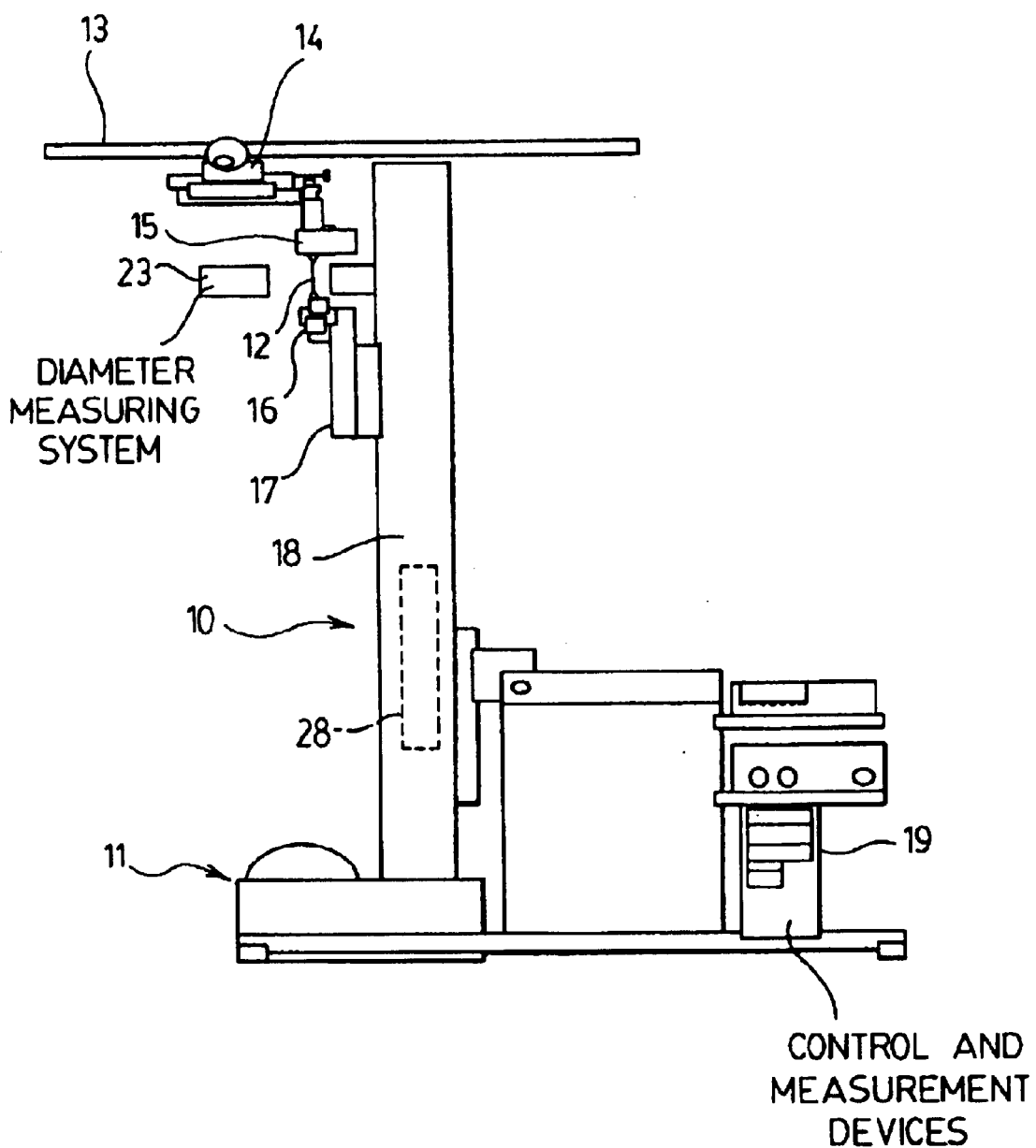
FIG. 1 is a schematic representation of a rheometer for measuring the elasticity of a fluid.
Figure 2:
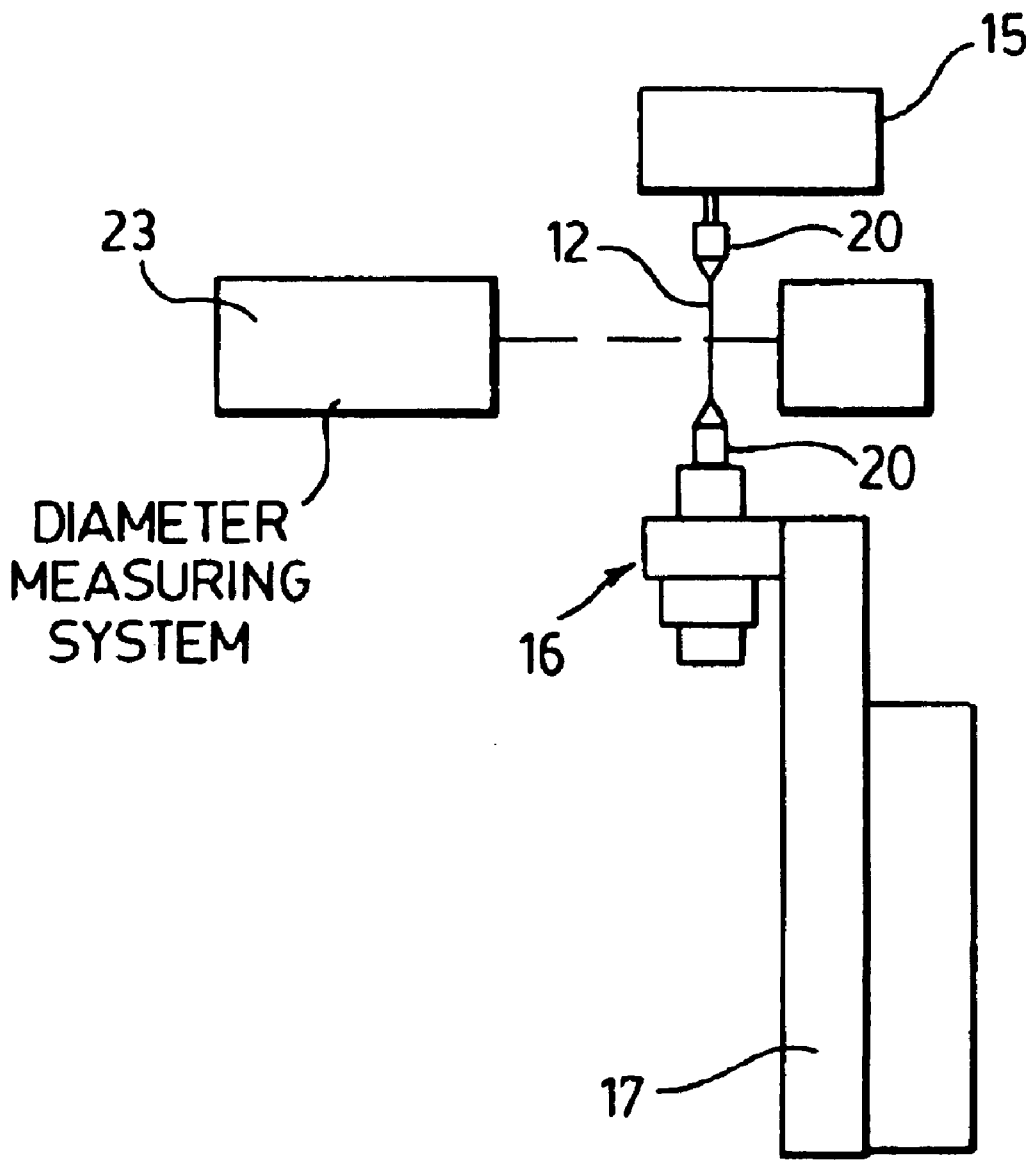
FIG. 2 is a schematic representation of specific components in the device of FIG. 1.

Referring to FIGS. 1 and 2, a rheometer 10 for measuring the elasticity of a fluid comprises a base 11 supporting a vertical track 18. A beam 13 projects to one side of the track 18 and carries an adjustable support 14 that is moveable and lockable in a horizontal plane. A carriage 17 is movably mounted on the vertical track 18 and can be moved along the track 18 by an actuator 28. A pair of platens 15, 16 are mounted on the support 14 and carriage 17 respectively. Each of the platens 15, 16 is a cylindrical disc having an exposed surface 20. The platens are maintained in a spaced relationship with the surfaces 20 facing each other so that a fluid sample 12 can be held between the surfaces 20 to provide a fluid bridge. The actuator 28 is controlled by control and measurement devices 19 to control the displacement of the carriage 17 along the track 14 to elongate the fluid bridge. A diameter measuring system 23 is located so as to provide diameter measurements of a fluid bridge formed between the platens 15, 16 at the midpoint of the fluid bridge. The measuring system is moved and controlled by control and measurement devices 19 so as to be maintained at the midpoint of the fluid bridge and provide a measurement of the diameter in real time.

Figure 3:
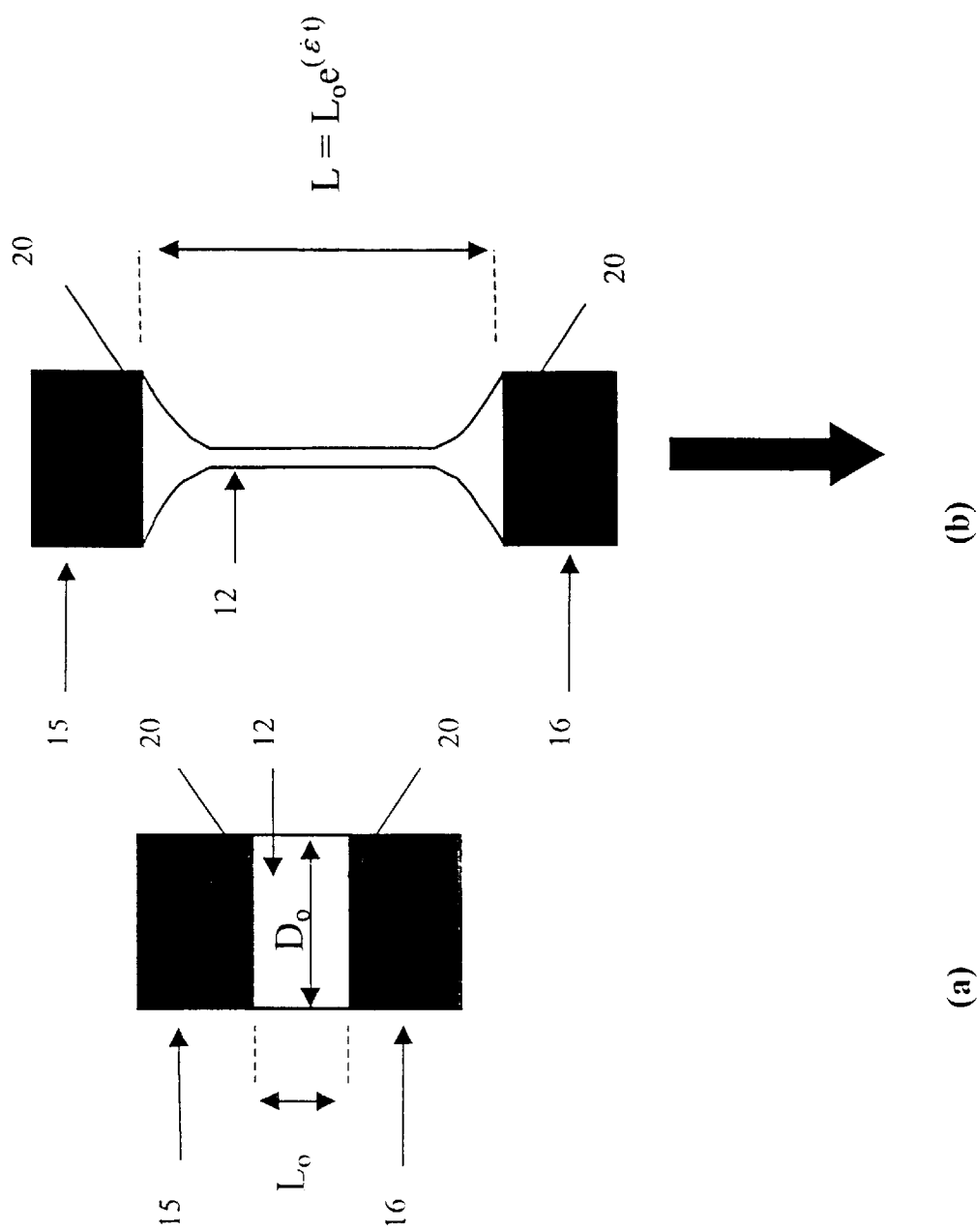
FIG. 3 is a schematic representation of the process of extensional deformation as performed by the device of FIGS. 1 and 2.

Referring to FIG. 3a, a fluid sample 12 is placed between opposed surfaces 20 of the platens 15, 16 to form a fluid bridge. As the platens separate, as shown in FIG. 3b, the fluid sample 12 between the platens 15, 16 is stretched to elongate the fluid bridge. The fluid bridge has an initial length $L_0$ and an initial diameter Do typically corresponding to the diameter D of the platens 15, 16. To measure the elasticity of the fluid sample 12, the platens are separated in a controlled and repeatable manner. Preferably they are separated at a constant extensional rate by the actuator 28, which means that the length of the fluid bridge, i.e. the separation distance L, is increasing exponentially with respect to time although other motions such as a constant velocity or a constant acceleration will also permit evaluation of elasticity. The diameter measuring system 23 measures the diameter of the fluid bridge in real time and a control and measurement device 19 keeps a record of the diameter of the fluid bridge 24 in real time. By reviewing the record of diameter with respect to time, the time when the fluid bridge breaks may be determined as a diameter measurement of zero. The elapsed time at which the break occurs indicates the displacement of the platen 16 from its initial position given the controlled movement of the actuator and this displacement is the breaking length $L_{max}$. Other ways of determining the extension at the break point may be utilised, such as direct measurement of the displacement of the platen 16 and other ways of determining the break of the fluid other than the diameter measuring technique may be used.

Figure 4:
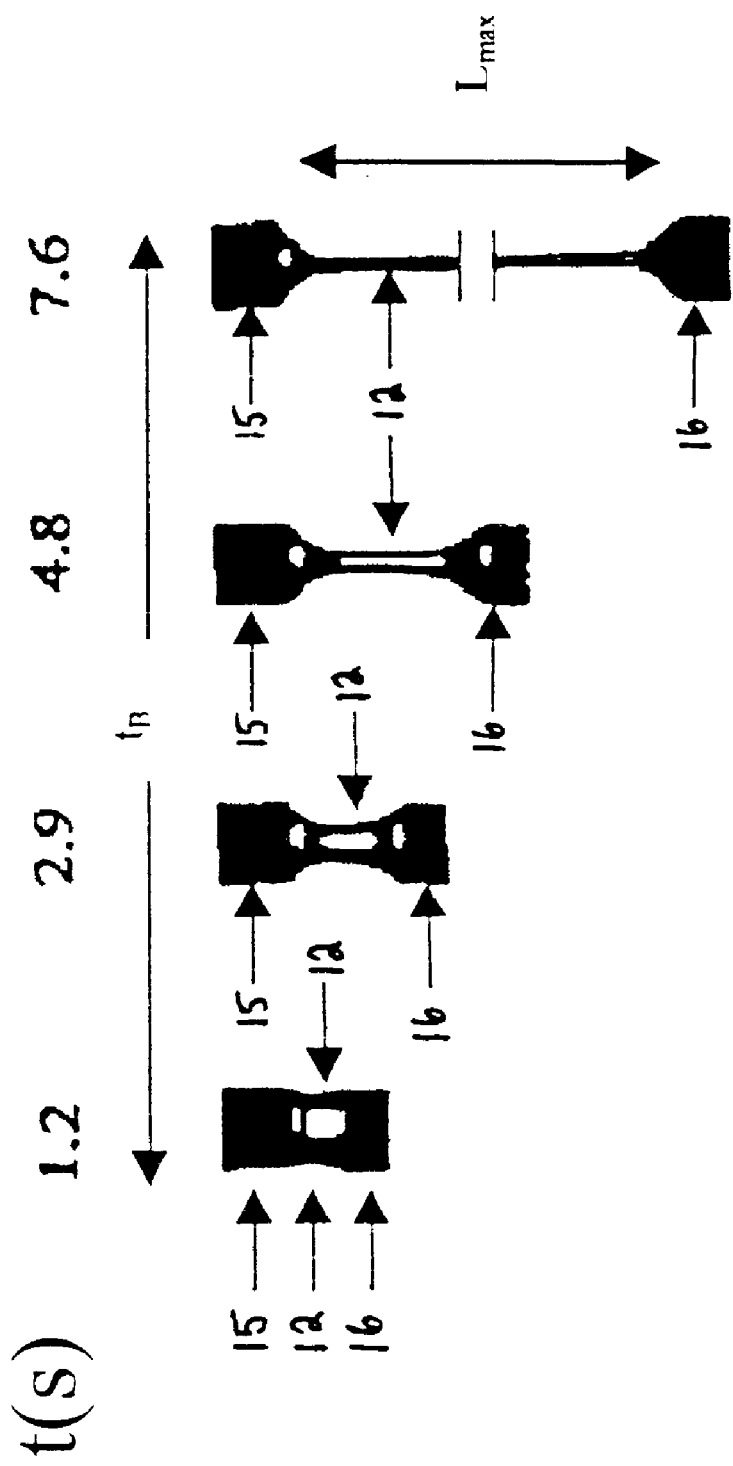
FIG. 4 is a schematic representation of the length of a fluid bridge of a highly elastic fluid at different time intervals.

The stretching of the sample at a constant rate of extension is shown in FIG. 4 where a fluid sample 12 is stretched at an extensional rate $\dot{\epsilon}$ from an initial length $L_0$ and initial diameter $D_0$ to a new length L and a new diameter d. The new length and diameter are theoretically related to the initial length and diameter by the relationships $L=L_0\exp(\dot{\epsilon}t)$ and $d=D_0\exp(-\tfrac{1}{2}\dot{\epsilon}t)$. That is, the length increases exponentially with time and the diameter decreases exponentially with time. In FIG. 4, the resultant fluid bridge 24 for an elastic fluid is shown at intervals of roughly 2 seconds from which it may be seen that the length of the fluid bridge increases exponentially with respect to time.

After a time, $t_B$ in FIG. 4, the fluid bridge breaks, as indicated by the gap, at which time the opposed surfaces 20 are a distance $L_{max}$ apart. The applicants have recognized that measurement of length at the break point may be used as an indicator of elasticity when compared with the breaking length of equivalent Newtonian fluids.

A measure of the elasticity of a fluid is the difference between the breaking strain of the fluid to the breaking strain of an equivalent Newtonian fluid. A measure of the breaking strain is a function of the ratio of $L_{max}/L_o$ that may conveniently be plotted as $\ln(L_{max}/L_0)$. Fluids are considered to be equivalent if values of a dimensionless group, of the form $$\frac{\sigma}{\eta\dot{\epsilon}D_o},$$

are equal at break point, for fluids subjected to a constant rate of extension, where $\sigma$ is the surface tension coefficient in N/m, $\eta$ is the viscosity in Pa·s, $\dot{\epsilon}$ is the extensional rate in $s^{-1}$ and $D_o$ is the initial diameter of the fluid bridge. Because the elasticity is relative to an equivalent Newtonian fluid, it is necessary to establish a Newtonian baseline or datum. This datum may be obtained from a plot of $\ln(L_{max}/L_0)$ versus $$\frac{\sigma}{\eta\dot{\epsilon}D_o},$$

or preferably as a plot of $\ln(L_{max}/L_0)$ versus $$\frac{\eta\dot{\epsilon}D_o}{\sigma},$$

a form of the dimensionless group known as the capillary number. This latter plot provides a plot in which increasing elasticity corresponds to an increasing value of the capillary number for non-Newtonian fluids.

Figure 5:
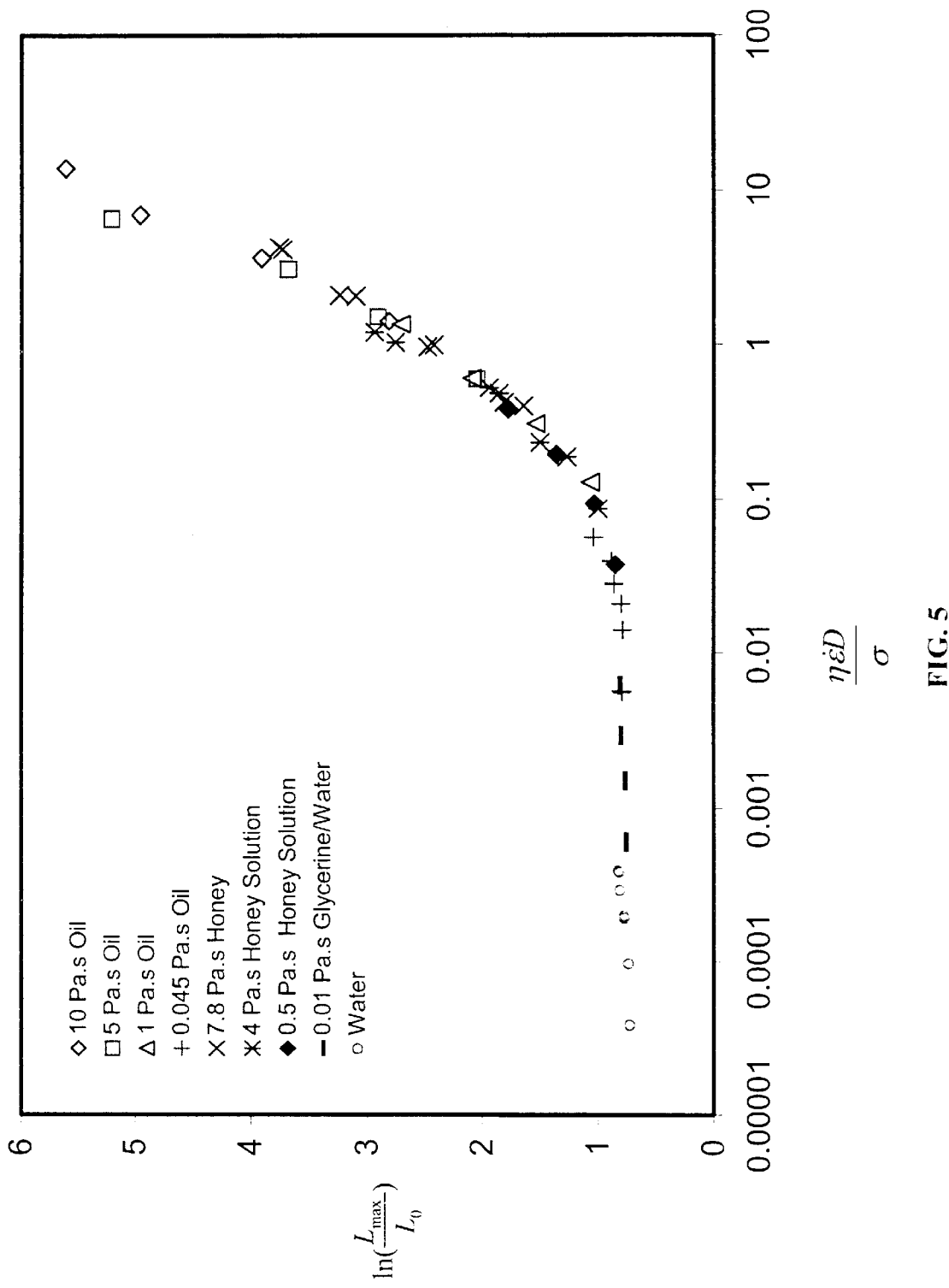
FIG. 5 is a plot showing the breaking length of Newtonian fluids when operated on by the device of FIGS. 1 and 2.

In one set of experimental results, the Newtonian datum was established by testing a range of inelastic oils and sugar solutions. The fluids were selected to have a range of viscosities and surface tension coefficients and each fluid was tested at several extensional rates. The datum, a plot of $\ln(L_{max}/L_0)$ versus $$\frac{\eta\dot{\epsilon}D_o}{\sigma}$$

is shown in FIG. 5 with fluids as indicated.

The experimental evidence indicates that the ratio of the breaking length $L_{max}$ of a Newtonian fluid to its initial length $L_0$, when plotted against a function of the dimensionless group $$\frac{\eta\dot{\epsilon}D_o}{\sigma},$$

provides a common curve for different Newtonian fluids. The different fluids exhibit similar results and provide a datum for the breaking lengths of Newtonian, i.e. inelastic, fluids.

Figure 6:
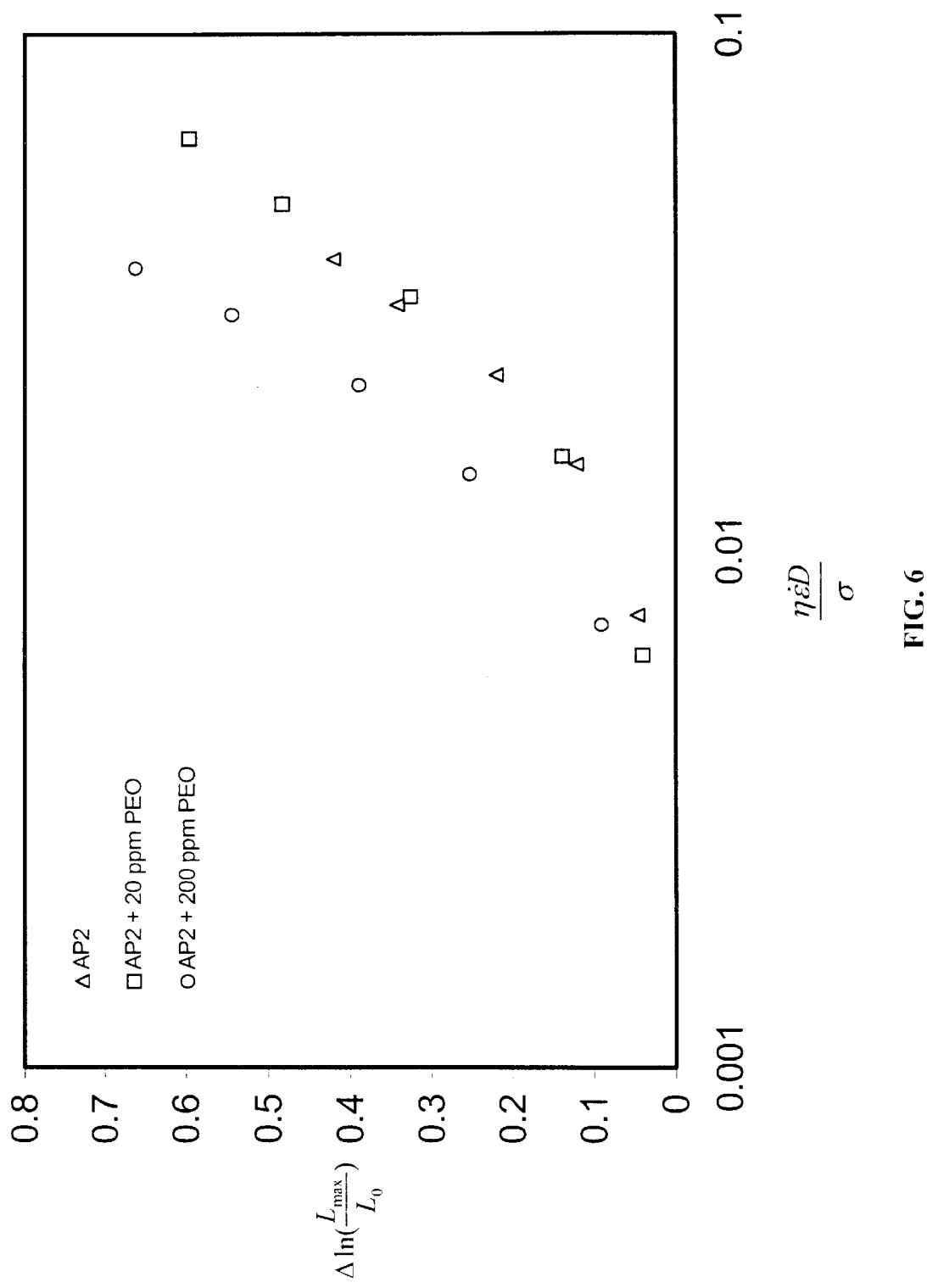
FIG. 6 is a plot of experimental results comparing the breaking lengths of three non-Newtonian fluids with equivalent Newtonian fluids.

When the same experiment is performed on a fluid known to exhibit elasticity, then the ratio $L_{max}/L_0$ changes. FIG. 6 shows the results of an experiment performed at different extensional rates $\dot{\epsilon}$ with each of three non-Newtonian fluids known to be moderately elastic. The results are plotted on FIG. 6 together with a best-fit curve representing the Newtonian datum of FIG. 5. The difference in breaking length between a test fluid and the Newtonian datum at a given capillary number is attributable to the elasticity of the fluid. Accordingly, the difference $\Delta$ may be used as a measure of the elasticity of the fluid.

To obtain the results shown in FIG. 6, a series of tests were conducted using an associative polymer solution, termed AP2, as an initial test fluid. This fluid is known to be moderately elastic and has a constant viscosity. The elasticity was determined for this type of fluid in the following manner.

From measurements with a viscometer, the viscosity was found to be 0.073 Pa·s, for shear rates from 1 to 20 $s^{-1}$.

The surface tension coefficient of AP2 was measured to be 0.060 N/m.

The initial sample diameter $D_o$ was 0.00308 m and the initial length $L_o$ was 0.00196 m. The sample was stretched out at an extensional rate of 2.0 $s^{-1}$ and the length $L_{max}$ when the fluid sample broke was measured to be 0.00455 m.

From these experimental results, the following calculations were made.

$$\ln\left(\frac{L_{max}}{L_0}\right) = \ln\left(\frac{0.00455}{0.00196}\right) = 0.842$$

$$\frac{\eta\dot{\epsilon}D_o}{\sigma} = \frac{(0.073)(2.0)(0.00308)}{0.060} = 0.0075$$

Further tests were conducted using extension rates of 4.0 $s^{-1}$, 6.0 $s^{-1}$, 8.0 $s^{-1}$ and 10.0 $s^{-1}$. A similar set of tests were conducted on the other two fluids.

For an equivalent Newtonian fluid, the data obtained from a best fit curve of the results shown in FIG. 5 provide values of breaking strain. At the value of $$\frac{\eta\dot{\epsilon}D_o}{\sigma}$$

of 0.0075 calculated above from the experimental data, the value of breaking strain for an equivalent Newtonian fluid is provided as:

$$\ln\left(\frac{L_{max}}{L_0}\right)_{Newtonian} = 0.793$$

The difference $\Delta$ in breaking strains is 0.842−0.793=0.049, which is therefore a measure of the elasticity of AP2.

Figure 7:
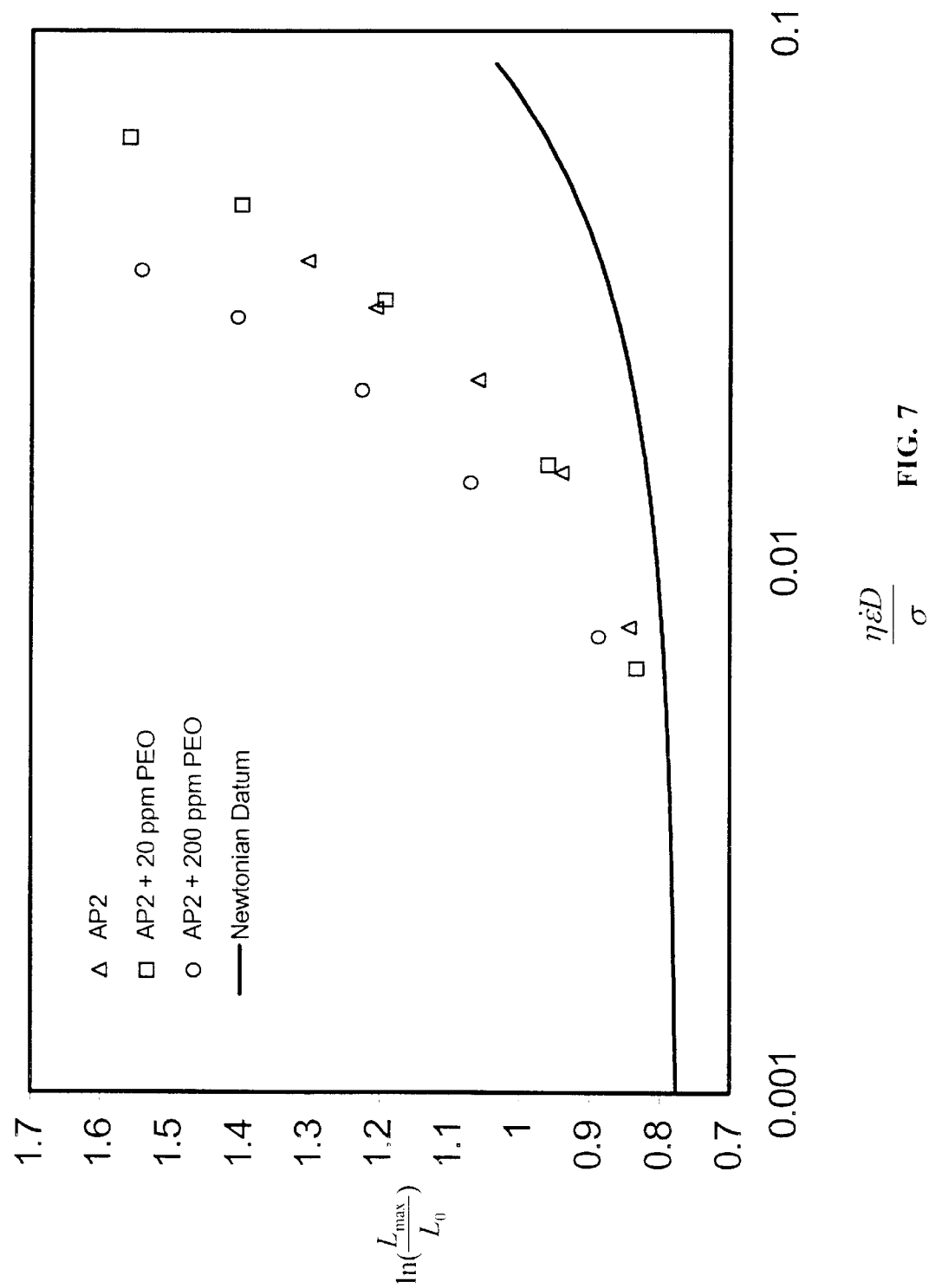
FIG. 7 is a plot of experimental results showing the difference in breaking strain of three non-Newtonian fluids when acted on by the device of FIGS. 1 and 2.

Further, the differences may be used directly to compare the elasticities of a number of samples. FIG. 7 is a plot of the differences of the breaking strains, $\Delta \ln(L_{max}/L_0)$, for the three fluids of FIG. 6, showing among other things the additional elasticity caused by the addition of 200 ppm of a polymeric additive PEO.

When a fluids is shear-thinning (i.e. the viscosity decreases with shear rate), the appropriate value of $\eta$ in $$\frac{\eta \dot{\varepsilon} D_o}{\sigma}$$

is not apparent, and may be found as follows. The relevant value of $\eta$ is the value just before the fluid bridge breaks. During that period, there is an effective extensional rate, which is found from the measurements of d(t) and the equation $$d(t) = D_0 \exp\left(-\frac{1}{2}\dot{\varepsilon}t\right).$$

The equivalent shear rate is $\sqrt{3}$ times this effective extensional rate and the relevant value of $\eta$ is at that shear rate.

The details of the calculation procedure are:

A viscometer was used to measure the viscosity of a shear-thinning fluid, termed Industrial Fluid 1 (IF1), over a range of shear rates. A line which fits the data was found to be given by the equation:

$$\eta = 14.46 \dot{\gamma}^{-0.864}, \text{ where } \dot{\gamma} \text{ is the shear rate.}$$

The surface tension coefficient of IF1 was measured to be 0.062 N/m.

The initial sample diameter was 0.00297 m and the initial length was 0.00197 m. The sample was stretched out at an extensional rate of 1.0 s$^{-1}$ and the length when the fluid sample broke was measured to be 0.00500 m. Therefore $$\ln\left(\frac{L_{max}}{L_0}\right) = \ln\left(\frac{0.00500}{0.00197}\right) = 0.931$$

The effective extensional rate when the fluid sample broke, as found from the diameter versus time plot, was 250 s$^{-1}$.

The equivalent shear rate is $\sqrt{3}(250) = 433$ s$^{-1}$.

From the viscosity-shear rate relationship, $\eta = 14.46(433^{-0.864}) = 0.076$ Pa·s.

Hence $$\frac{\eta \dot{\varepsilon} D_o}{\sigma} = \frac{(0.076)(1.0)(0.00296)}{0.062} = 0.00363$$

For an equivalent Newtonian fluid, from the Newtonian datum at the same value of $$\frac{\eta \dot{\varepsilon} D_0}{\sigma}, \ \ln\left(\frac{L_{max}}{L_0}\right)_{Newtonian} = 0.781.$$

The difference in breaking strains is 0.931−0.781=0.150, which is therefore a measure of the elasticity of IF1.

Figure 8:
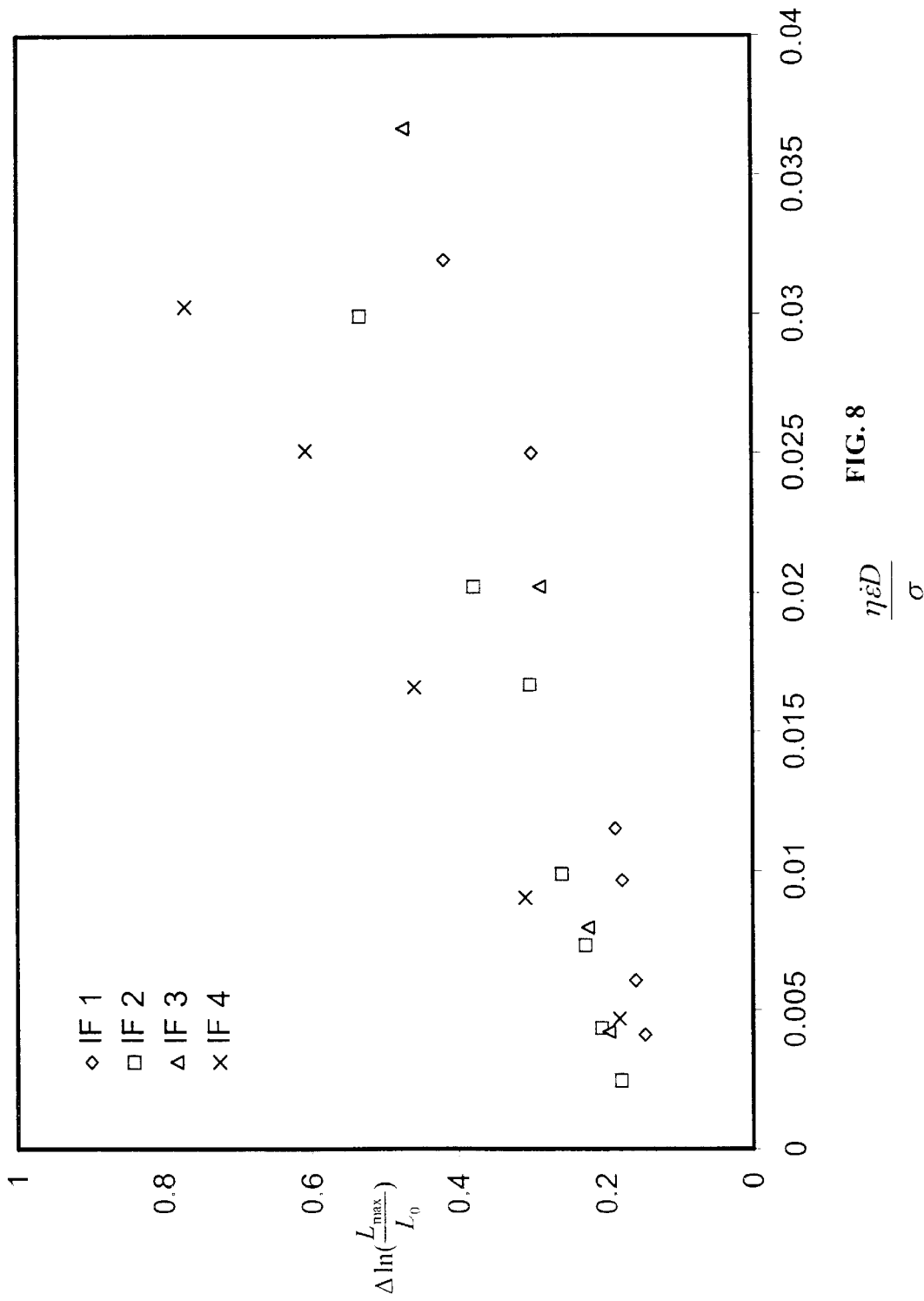
FIG. 8 is an experimental result comparing the breaking lengths of four industrial fluids.

Similar tests were performed in an experiment on four industrial fluids, IF 1, 2, 3 and 4 as shown in FIG. 8. The differences in the results obtained shows that the four fluids have different degrees of elasticity.

Figure 9:
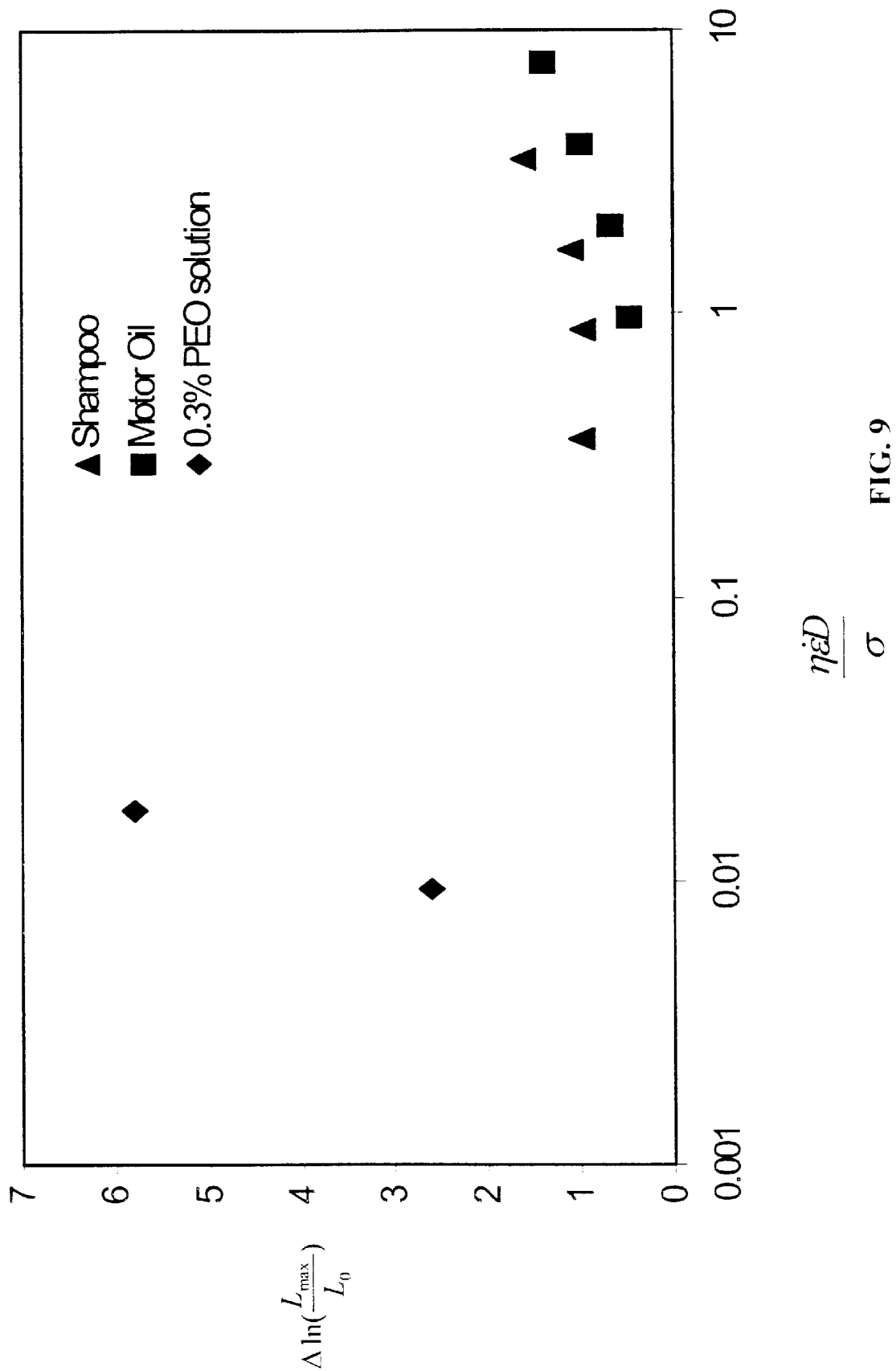
FIG. 9 is an experimental result comparing the breaking lengths of commonplace fluids to a laboratory fluid.

In further testing illustrated in FIG. 9, an experiment compared two commonplace fluids, namely a shampoo and a motor oil, to a laboratory fluid 0.3% PEO solution. It may be seen that the laboratory fluid is far more elastic than the shampoo and motor oil. Further, the shampoo is more elastic than the motor oil.

Figure 10:
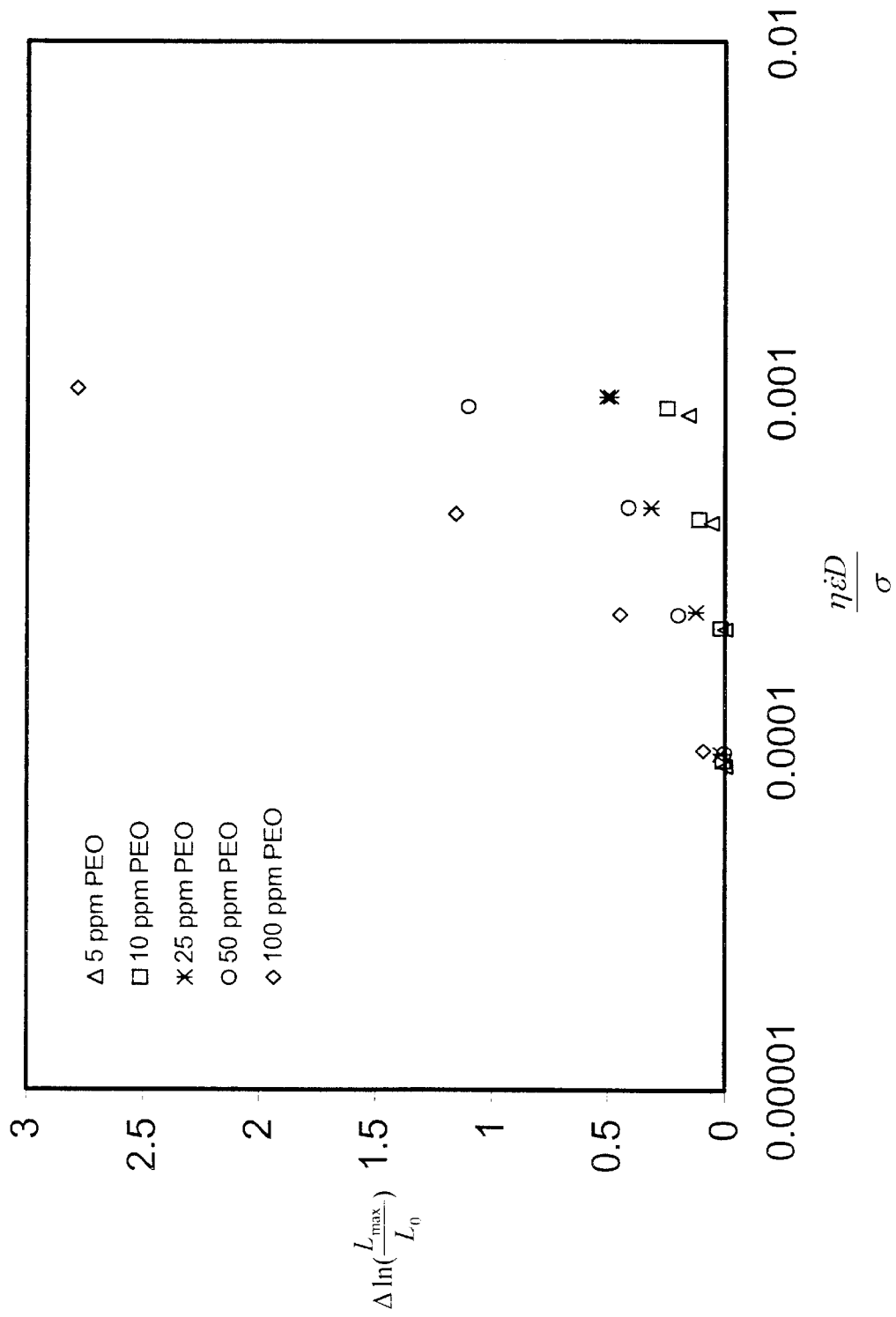
FIG. 10 is an experimental result comparing the breaking lengths of five laboratory fluids with varying amounts of a polymeric additive.

Referring to FIG. 10, an experiment on five laboratory fluids is shown. The breaking length correlates in an expected way to the different amounts of the polymeric additive PEO in the fluid, which is directly related to the elasticity of the fluid.

Accordingly, the results obtained indicate that the elasticity of a fluid may be measured by determining the extension of the fluid at which the break point of the fluid occurs. From the break point, an indicator of the relative elasticity may be obtained directly or an absolute measure obtained with reference to a datum for Newtonian fluids.

The above examples have been described with reference to a constant rate of extension for the sample. As noted above, other motions will vary depending on the motion but will include the relationship $$\frac{\eta}{\sigma}$$

and a function which has units of velocity. In the case of a constant velocity of separation, the dimensionless group will have the form $$\frac{\eta V}{\sigma}$$

where V is the separation velocity. In the case of constant acceleration, the group will have the form $$\frac{\eta}{\sigma}\sqrt{aD}$$

where a is the rate of acceleration of separation.

In each case, a comparison of the results obtained with different fluids will indicate the relative elasticity and a comparison with a Newtonian fluid will provide an absolute measure of elasticity.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A method for determining the elasticity of a fluid comprising the steps of:
    a) locating a sample of said fluid to form a fluid bridge between a pair of relatively moveable surfaces,
    b) extending said fluid bridge in a controlled manner,
    c) continuing extension of said fluid bridge to determine an extension of said fluid bridge at a break point thereof,
    d) utilizing said extension at the break point as an indicator of the elasticity of the fluid.

2. A method according to claim 1 wherein said extension continues until the break point of said fluid bridge is reached.

3. A method according to claim 1 including the step of locating the sample between a pair of opposed surfaces and moving said surfaces relative to one another in a controlled manner to form said fluid bridge.

4. A method according to claim 3 wherein said opposed surfaces are moved relative to one another at a constant rate of extension of said fluid bridge.

5. A method according to claim 3 wherein said opposed surfaces are moved relative to one another at a constant velocity.

6. A method according to claim 3 wherein said opposed surfaces are removed relative to one another at a constant rate of acceleration.

7. A method according to claim 3 including the step of comparing the initial displacement of said surfaces to the displacement of said surfaces at the break point to obtain an indication of the elasticity.

8. A method according to claim 1 wherein said indicator of elasticity is provided by comparing behavior said sample fluid to that of an equivalent Newtonian fluid.

9. A method according to claim 8 wherein a datum for an equivalent Newtonian fluid is obtained from tests conducted on a plurality of Newtonian fluids.

10. A method according to claim 1 wherein said extension at said break point is determined by measuring the time that elapses from initiating movement of said surfaces to the break point of said fluid sample.

11. An apparatus for measuring the elasticity of a fluid, comprising:

a) a pair of opposed surfaces spaced apart for holding a sample of said fluid therebetween and thereby form a fluid bridge of said fluid;

b) an actuator coupled to at least one of said pair of surfaces to provide a relative displacement between said surfaces to extend said fluid bridge in a controlled manner;

c) a measuring system for determining the displacement of said surfaces at a position corresponding to a point at which said fluid bridge breaks and d) an indicator to indicate said displacement and thereby provide an indication of the elasticity of said sample.

12. An apparatus according to claim 11 wherein said measuring system includes a diameter measuring device to monitor the minimum diameter of said fluid sample during extension thereof.

* * * * *